United States Patent

Castello Escude et al.

(10) Patent No.: US 8,257,245 B2
(45) Date of Patent: Sep. 4, 2012

(54) ADJUSTABLE SLING AS A SUPPORT OF INTERNAL ORGANS OR ANATOMICAL TISSUES

(75) Inventors: Antoni Castello Escude, Terrassa (ES); Francisco Farrer Velazquez, Calatayud (ES)

(73) Assignee: Specialties Remeex International, S.L., Terrassa (ES)

( * ) Notice: Subject to any disclaimer, the term of this patent is extended or adjusted under 35 U.S.C. 154(b) by 1163 days.

(21) Appl. No.: 11/490,136

(22) Filed: Jul. 21, 2006

(65) Prior Publication Data

US 2008/0021356 A1 Jan. 24, 2008

(51) Int. Cl.
*A61F 2/00* (2006.01)
(52) U.S. Cl. ............... 600/37; 600/30; 606/151
(58) Field of Classification Search ............ 600/29–31, 600/37
See application file for complete search history.

(56) References Cited

U.S. PATENT DOCUMENTS

| | | | | |
|---|---|---|---|---|
| 6,042,534 | A * | 3/2000 | Gellman et al. | 600/30 |
| 6,612,977 | B2 * | 9/2003 | Staskin et al. | 600/30 |
| 7,083,637 | B1 | 8/2006 | Tannhauser | |
| 7,448,186 | B2 * | 11/2008 | Siniaguine | 53/513 |
| 2002/0099260 | A1 * | 7/2002 | Suslian et al. | 600/30 |
| 2004/0144394 | A1 * | 7/2004 | Dauner et al. | 128/885 |
| 2005/0240076 | A1 * | 10/2005 | Neisz et al. | 600/30 |
| 2005/0277806 | A1 * | 12/2005 | Cristalli | 600/30 |
| 2006/0089525 | A1 * | 4/2006 | Mamo et al. | 600/37 |
| 2006/0195011 | A1 * | 8/2006 | Arnal et al. | 600/37 |

\* cited by examiner

*Primary Examiner* — Charles A Marmor, II
*Assistant Examiner* — Catherine E Burk
(74) *Attorney, Agent, or Firm* — Dowell & Dowell, P.C.

(57) ABSTRACT

Adjustable sling as a support of internal organs or anatomical tissues that can be properly positioned into the patient's body without any special instrument, just by using a standard surgical forceps, and it allows to be repositioned, which is provided with a cavity in each of the laterals of the sling, with an opening to be able to introduce a standard surgical forceps to push the sling into the target place, said cavities formed by folding a part of the extremes of the sling inwards and after that sealing them by thread knots or thermal fixation.

11 Claims, 4 Drawing Sheets

ADJUSTABLE SLING AS A SUPPORT OF INTERNAL ORGANS OR ANATOMICAL TISSUES

BACKGROUND OF THE INVENTION

1. Field of the Invention

The present invention consist of an "Adjustable sling as a support of internal organs or anatomical tissues" with a particular design and construction that provides the sling a maximum efficiency.

The design and configuration of the sling permits and facilitates its implantation in the patient's body, near the place to be treated, as an organ or anatomical tissue suspension or traction system minimizing the complications.

2. Brief Description of the Related Art

There are in the market various elements, principally slings, which are positioned as a hammock to elevate or support organs to improve its functioning.

As an example there are the U.S. Pat. No. 6,960,160,/U.S. Pat. No. 6,478,727/U.S. Pat. No. 6,491,703.

Specifically, U.S. Pat. No. 6,960,160 presents a "method for treating female urinary incontinence" that uses some hooks to anchor a sling to the tissue and special needles to position the hooks into the tissues.

Specifically, U.S. Pat. No. 6,478,727 presents a "percutaneous device and method for treating urinary stress incontinence in women using a sub urethral tape" that uses special instruments to position a long sling from the vaginal wall to the abdominal wall.

Specifically, U.S. Pat. No. 6,491,703 presents a "surgical instrument for treating female urinary incontinence" that uses special needles to place a long sling from the vaginal wall to the abdominal wall.

In all precedents the slings that support an anatomical tissue or organ need special instruments to be placed, such as threads, needles, or hooks, to place and maintain the sling in right position.

SUMMARY OF THE INVENTION

The objective of the invention is a short sling that will be properly positioned into the patient's body without any special instrument, just by using a standard surgical forceps, and will be able to be repositioned, if needed, with the same methods used to place it.

For this purpose, the sling has been designed in a way that is provided with a cavity in each lateral side, with an opening to be able to introduce a standard surgical forceps to push the sling into place, up to the desired position. Said cavities are formed by folding a part of the extremes of the sling inwards and after that sealing them at least from the upper and lower folded edges by thread knots or thermal fixation. Additionally, the edge corresponding to the folding axis can be also sealed. Another sealing method can be used to shape the extreme cavities of the sling.

The sling extremes can be wider than the body of the sling, so the surgical forceps can push the sling in whatever direction.

The sling cavities have double sling layer, thus stimulating the tissue ingrowths and the tissue anchorage of the sling without any additional anchoring hook or special device.

Additionally in the sling central part two traction threads are arranged, which in combination with the surgical forceps and the sling cavities allow the proper positioning of the sling. By pulling the central traction threads during the sling introduction, there is a limit of the space that the sling will penetrate in the body, avoiding thus involuntary injuries like surgeons may have with other slings like organ or vessels perforation.

Among other applications, the sling can be used for urinary incontinence, pelvic floor prolapse abdominal organs prolapse, thoracic organs prolapse, and anatomical tissue repositioning in any part of the body.

Details and features are provided during the description together with the drawings that are included as illustrative, but non-limitative information of the invention.

A list of the various references used to describe the embodiments carried out on the sling of the present invention follows: (10) sling, (11) sling body; (12) central part of the sling; (13) extreme zones; (13a) folded part; (13a) part; (14) axis; (15) traction threads; (16) cavities; (17) cavity seams; (18) surgical forceps; (19) tips of the surgical forceps; (20) upper and lower edges; extreme edge (21); open knots (22); and openings (23).

DESCRIPTION OF THE PREFERRED EMBODIMENT

Figure 1:
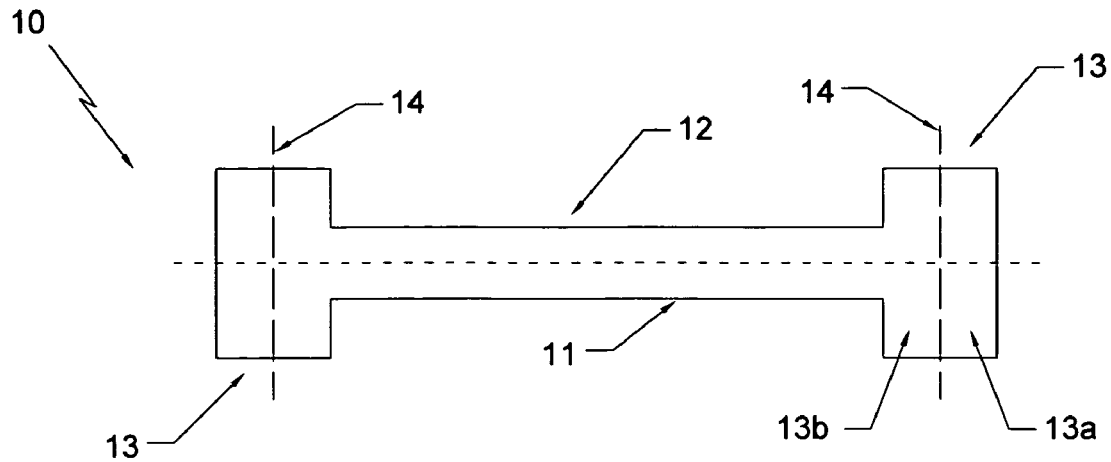
FIG. 1 is a superior view of the sling (10) with its extremes zones (13) being extended, before the folding of the folded zone (13a) by the ideal axis (14) over the zone (13b).

In a preferred design of the invention, the sling (10) is made of a monofilament polypropylene provided with a central zone (12) and wider extremes than the central zone, like is shown in FIG. 1.

Figure 2:
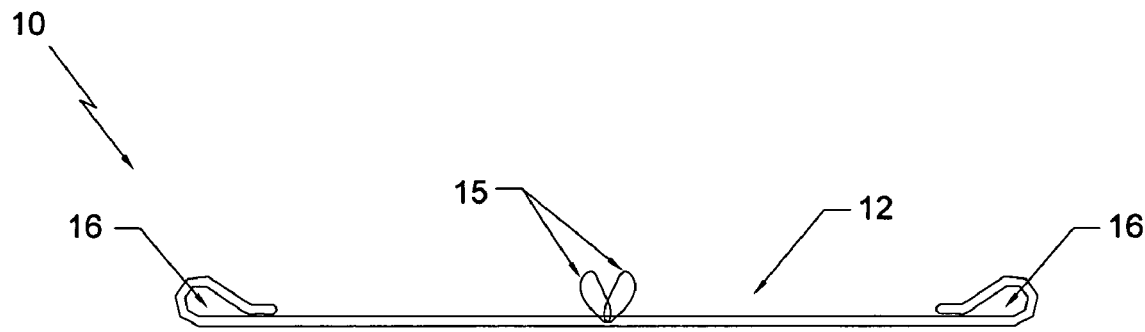
FIG. 2 is a frontal view of the sling (10) with its extreme zones 13 being already folded, so forming pockets which define the cavities (16) which are accessible by a standard surgical forceps.
Figure 3:
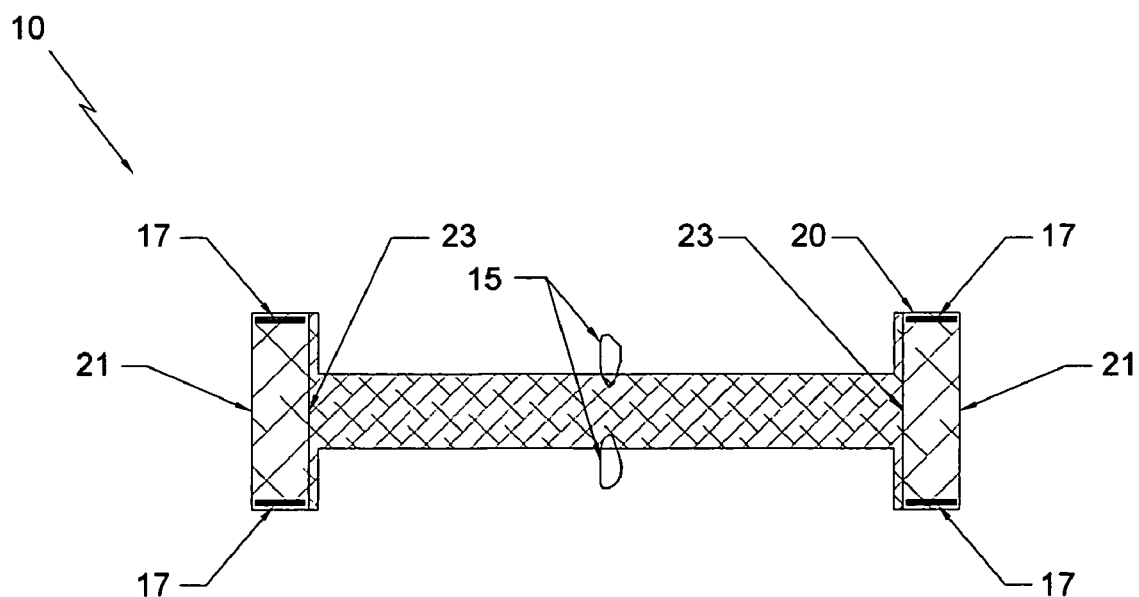
FIG. 3 is a superior view of the sling (10) with its extremes (13) being already folded and sealed with two welding seams (17).
Figure 4:
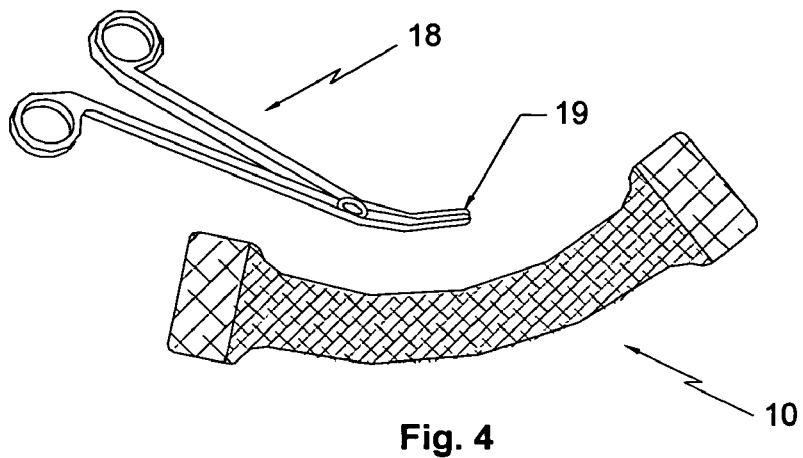
FIG. 4 is a view of the sling (10) and a standard surgical forceps (18).
Figure 5:
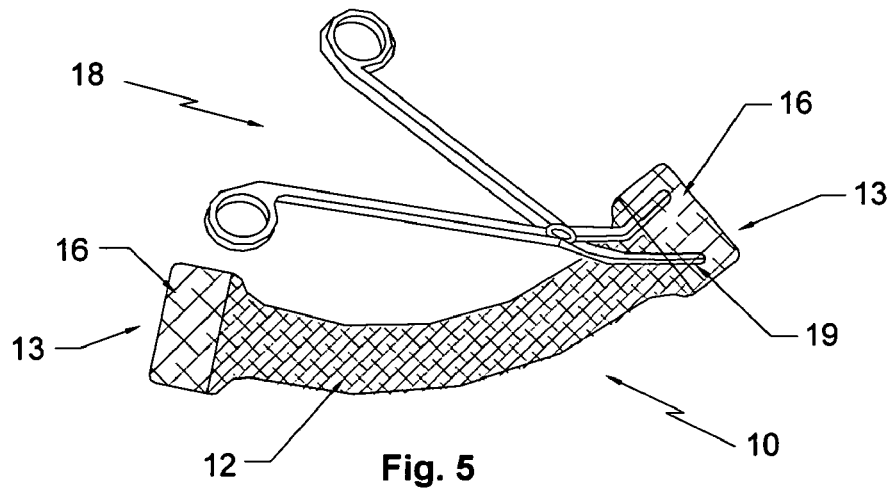
FIG. 5 is a view of the sling (10) with the surgical forceps tips (19) fully extended inside one of the sling cavities (16).
Figure 6:
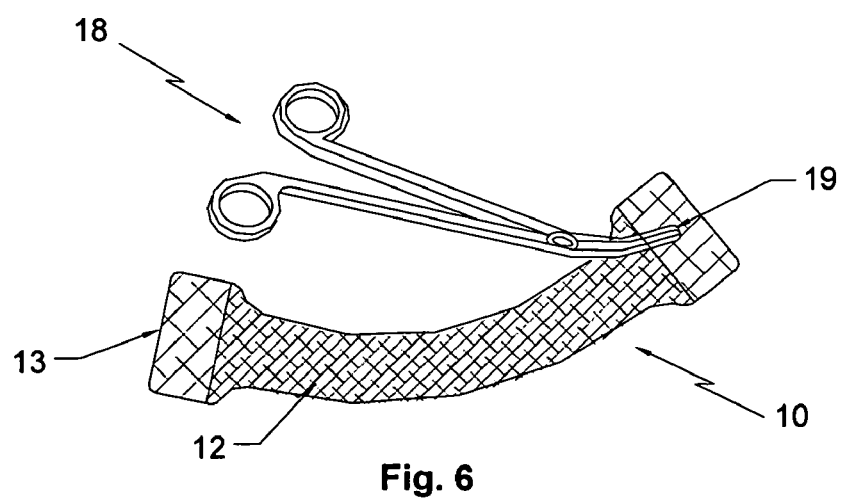
FIG. 6 is a view of the sling (10) with its cavity (16) collapsed by the surgical forceps (18) to be introduced in the body.
Figure 7:
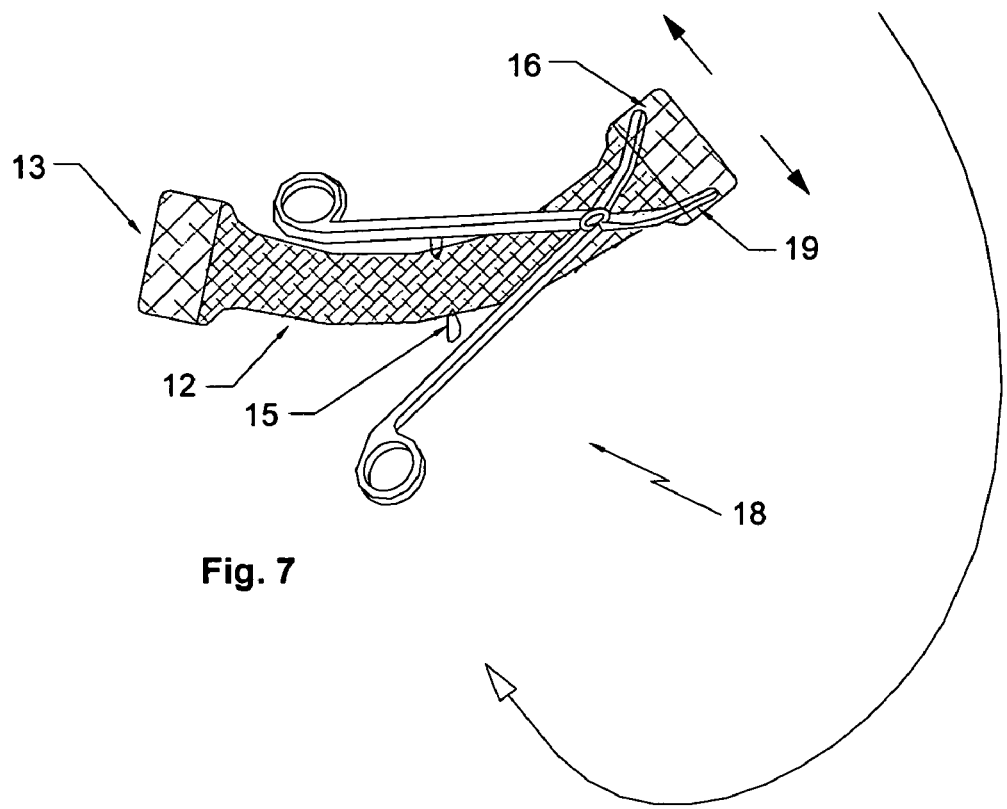
FIG. 7 is a view of the sling (10) with the standard surgical forceps (18) reopening the sling cavity (16) once introduced to the body in order to increase the fibrosis surface and the sling anchorage.

In reference again to FIG. 1, the folded parts (13a) are folded inwards by the ideal axis (14) over the parts (13b), so forming pockets defining the sling cavities (16) which are open toward the central portion of the sling, as shown in FIGS. 2 and 3.

Said folded parts (13a) are maintained over the other parts (13b) by means of two thermal seals (17): one sealing the upper edge and another sealing the lower edge (20) of the folded extremes (13a), as represented in FIG. 3. Additionally, the extreme edge (21) corresponding to the axis can be also sealed. Therefore, the cavities (16) have a rectangular configuration with an opening (23) that allows the surgeon to introduce inside the surgical forceps (18).

The geometry of the cavities (16) can also adopt other similar configurations, as long as it permits the easy and correct introduction of standard surgical forceps to push and drive the sling to the proper position.

As represented in FIG. 2, the sling (10) incorporates two traction threads (15) in the centre of the body (11) of the sling (10) to hold the sling (10) when inserting it into the body and to avoid its penetration too far. By playing with the surgical forceps (18) and the traction threads (15) the sling (10) can be positioned with maximum control, so avoiding dangerous structures.

Figure 8:
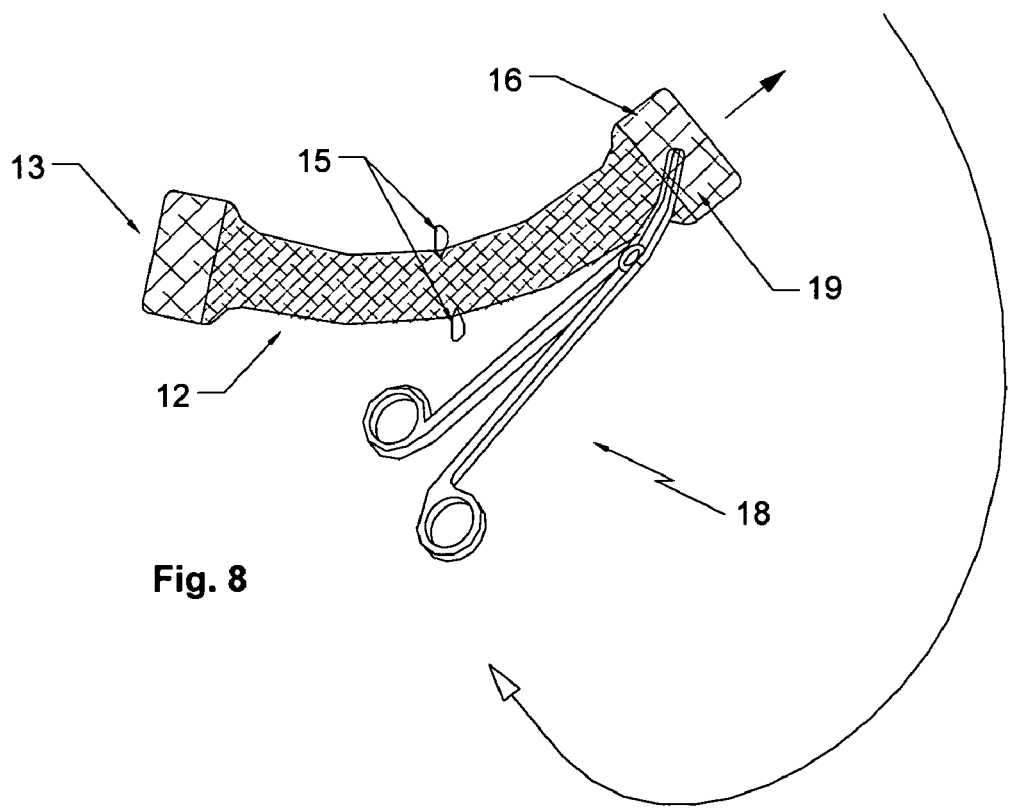
FIG. 8 is a view of the sling (10) of how the surgical forceps (18) can be reintroduced in the sling cavity (16) to readjust the sling position in the body.

The possibility of repositioning the sling (10) into the interior of the patient's body is not only during the surgery, but also during a period of time of 72 hours after the surgical implantation, before the sling is fully integrated into the patient's tissue by a fibrosis process. This repositioning can be made by reintroducing the surgical forceps (18) into the cavity of the sling (16) and pushing it further or by pulling the traction threads (15) of the central part of the sling (10), as shown in FIG. 8.

Figure 9:
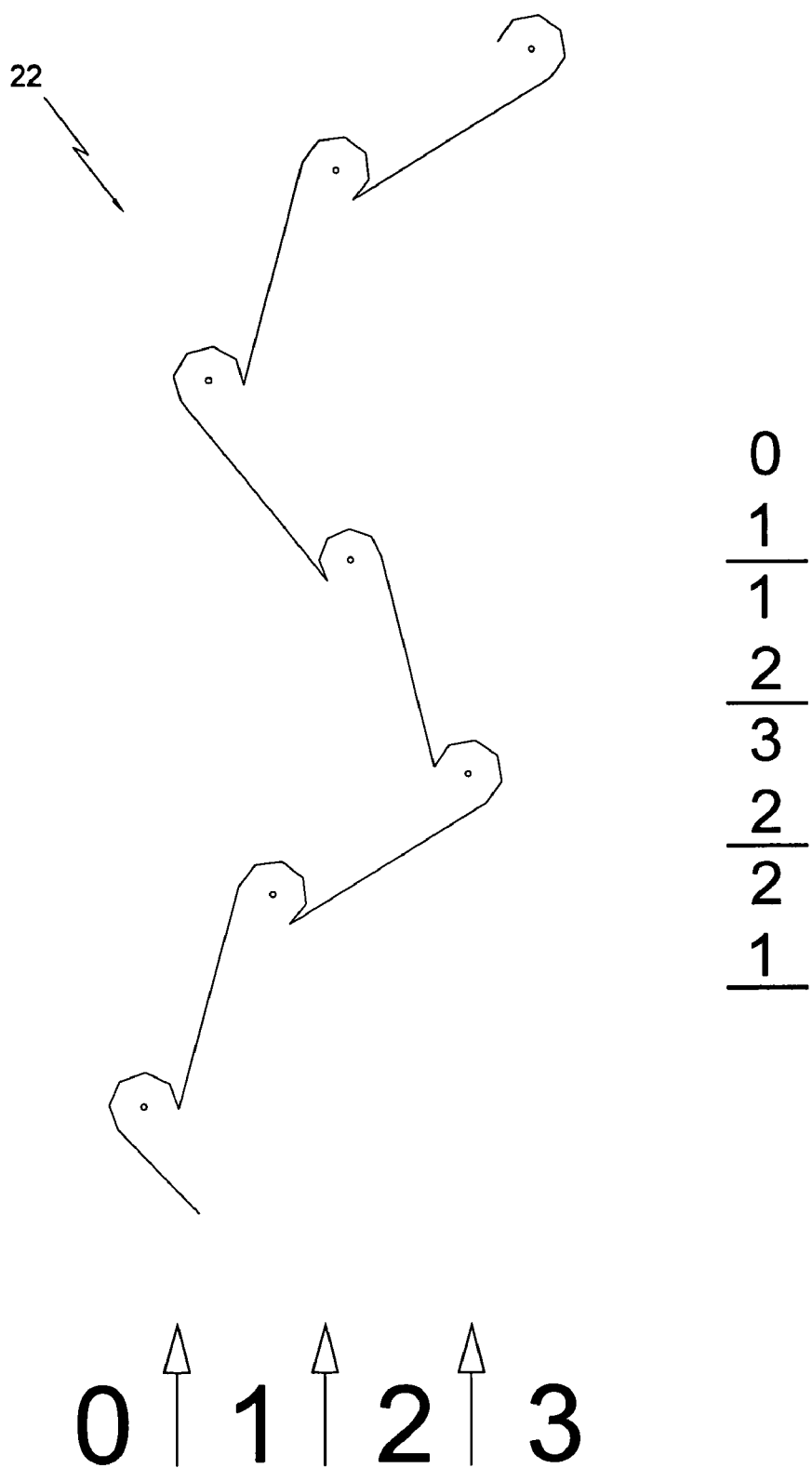
FIG. 9 is a view of a preferred design of an open knot (22) for the construction of the sling (10).

In order to avoid infections in this and any kind of mesh implanted in patient's body, a special mesh construction has been developed to manufacture the sling (10). The special characteristic of the new mesh is that it has open knots (22), as shown in FIG. 9.

In order to implant said mesh with open knots (22) in the patient's body, this mesh advantageously offers no place for bacteria nesting. There is no micro interstitial space into any knot; so this gives the macrophages always the possibility to reach whatever bacteria is over the mesh (10).

Accordingly, the scope of the present invention is not limited to the specific embodiments as illustrated herein, but is limited only by the following claims and equivalents thereof.

The invention claimed is:

1. An adjustable sling for supporting organs or anatomical tissue comprising a sling body provided with a central portion and opposite end portions, the opposite end portions being formed to define at least partially closed and opposing pockets, each pocket defining an internal cavity and having an opening into the cavity oriented toward the central portion, and the openings and cavities being of a size to permit an end of a surgical forceps to be inserted into the cavities to adjust a position of the sling body during surgical implantation, traction threads secured to extend outwardly from opposite edges in an area of a center of the central portion of the sling body and which are manipulable to limit penetration of the sling into a patient during implantation of the sling, wherein the opposing pockets having cavities for receiving the surgical forceps are wider than the central portion of the sling body, and wherein the pockets are formed by folding opposite ends of the sling body over adjacent portions of the sling body and toward the central portion thereof such that upper and lower generally parallel edges are formed on opposite sides of the openings into the pockets such that the cavities are generally rectangular in configuration.

2. The adjustable sling according to claim 1, wherein the upper and lower edges are closed and sealed by thread knots.

3. The adjustable sling according to claim 1, wherein the upper and lower edges being closed and secured by thermal seals.

4. The adjustable sling according to claim 1, wherein the sling is made of a biocompatible material.

5. The adjustable sling according to claim 1, wherein the pockets are made of a biocompatible material different from material used for the central portion of the sling body.

6. The adjustable sling according to claim 1, wherein the sling is formed of a mesh material defined having open knots at the intersection of the threads.

7. The adjustable sling according to claim 1, wherein the sling is configured to support a urethra for urinary incontinence patients.

8. The adjustable sling according to claim 1, wherein the sling is configured for pelvic floor prolapse.

9. The adjustable sling according to claim 1, wherein the sling is configured for abdominal prolapse.

10. The adjustable sling according to claim 1, wherein the sling is configured for thoracic prolapse.

11. The adjustable sling according to claim 1, wherein the sling is configured for repositioning of facial tissue.

* * * * *